(12) United States Patent
Graham et al.

(10) Patent No.: US 7,849,978 B2
(45) Date of Patent: Dec. 14, 2010

(54) BRAKE SYSTEM FOR PATIENT CARE EQUIPMENT SUPPORT ARM

(75) Inventors: Mark Alan Graham, Springboro, OH (US); Christian H. Reinke, York, SC (US)

(73) Assignee: Hill-Rom Services, Inc., Wilmington, DE (US)

( * ) Notice: Subject to any disclaimer, the term of this patent is extended or adjusted under 35 U.S.C. 154(b) by 452 days.

(21) Appl. No.: 10/575,211

(22) PCT Filed: Oct. 12, 2004

(86) PCT No.: PCT/US2004/033648

§ 371 (c)(1),
(2), (4) Date: Apr. 10, 2006

(87) PCT Pub. No.: WO2005/037166

PCT Pub. Date: Apr. 28, 2005

(65) Prior Publication Data

US 2007/0067911 A1    Mar. 29, 2007

Related U.S. Application Data

(60) Provisional application No. 60/510,756, filed on Oct. 13, 2003.

(51) Int. Cl.
*F16D 51/00* (2006.01)

(52) U.S. Cl. .................... 188/74; 188/72.1; 188/77 W; 188/171; 5/600; 248/122.1; 248/281.11; 248/282.1

(58) Field of Classification Search .................. 188/74, 188/171, 72.9, 77 W, 170, 72.1; 248/122.1, 248/125.7, 281.11; 5/600, 658, 503.1
See application file for complete search history.

(56) References Cited

U.S. PATENT DOCUMENTS

| 2,560,884 | A | 7/1951 | Nagourney |
| 4,185,801 | A | 1/1980 | Plymoth |
| 4,307,672 | A | 12/1981 | Shikimi |
| 4,359,207 | A | 11/1982 | Maryonovich et al. |
| 4,475,322 | A | 10/1984 | Russo et al. |

(Continued)

FOREIGN PATENT DOCUMENTS

DE    2 061 662    6/1972

(Continued)

OTHER PUBLICATIONS

The ondaScope™ ceiling suspension stand, Modular design, Flexibility, Ondal Industrietechnik GmbH brochure, Jul. 11, 1996.

(Continued)

*Primary Examiner*—Robert A Siconolfi
*Assistant Examiner*—Mariano Sy
(74) *Attorney, Agent, or Firm*—Barnes & Thornburg LLP

(57) ABSTRACT

A patient care equipment support system includes an arm supported in a hospital room for pivoting movement about a generally vertical axis, a patient care equipment column coupled to the arm for movement therewith, and a brake configured to impede the pivoting movement of the arm. The brake allowing the pivoting movement of the arm when the brake is deactivated in response to a user input. The column is configured to support patient care equipment.

21 Claims, 3 Drawing Sheets

U.S. PATENT DOCUMENTS

| | | | |
|---|---|---|---|
| 4,487,389 A | | 12/1984 | Ziegler |
| 4,548,373 A | | 10/1985 | Komura |
| 4,687,167 A | | 8/1987 | Skalka et al. |
| 4,725,027 A | | 2/1988 | Bekanich |
| 4,742,980 A | | 5/1988 | Heigl |
| 4,759,048 A | * | 7/1988 | Ohlson ......................... 378/197 |
| 4,836,478 A | | 6/1989 | Sweere |
| 4,945,592 A | | 8/1990 | Sims et al. |
| 4,993,683 A | | 2/1991 | Kreuzer |
| 4,997,155 A | | 3/1991 | Reuter et al. |
| 5,026,017 A | | 6/1991 | Kreuzer |
| 5,037,267 A | | 8/1991 | Warner et al. |
| 5,040,765 A | | 8/1991 | Schonfelder |
| 5,108,064 A | | 4/1992 | Kreuzer |
| 5,126,928 A | | 6/1992 | Hughes |
| 5,135,191 A | | 8/1992 | Schmuhl |
| 5,265,701 A | | 11/1993 | Ogasawara et al. |
| 5,306,109 A | | 4/1994 | Kreuzer et al. |
| 5,332,181 A | * | 7/1994 | Schweizer et al. ..... 248/123.11 |
| 5,366,191 A | | 11/1994 | Bekanich |
| 5,375,049 A | | 12/1994 | Witt |
| 5,396,673 A | | 3/1995 | Foster |
| 5,452,807 A | | 9/1995 | Foster et al. |
| 5,455,975 A | * | 10/1995 | Foster ........................... 5/600 |
| 5,480,212 A | | 1/1996 | Marconet |
| 5,490,652 A | | 2/1996 | Martin |
| 5,527,125 A | | 6/1996 | Kreuzer et al. |
| 5,560,583 A | | 10/1996 | Holmgren |
| 5,618,090 A | | 4/1997 | Montague et al. |
| 5,655,741 A | | 8/1997 | Watkins |
| 5,876,016 A | | 3/1999 | Urban et al. |
| 6,036,147 A | | 3/2000 | Militzer |
| 6,056,249 A | | 5/2000 | Fillon, Jr. |
| 6,095,468 A | | 8/2000 | Chirico et al. |
| 6,109,572 A | | 8/2000 | Urban et al. |
| 6,213,481 B1 | | 4/2001 | Marchese |
| 6,364,268 B1 | | 4/2002 | Metelski |
| 6,471,165 B2 | * | 10/2002 | Twisselmann ......... 248/123.11 |
| 6,513,630 B1 | | 2/2003 | Nakagomi |
| 6,817,585 B2 | | 11/2004 | Wagner et al. |
| 7,040,057 B2 | | 5/2006 | Gallant et al. |
| 7,065,811 B2 | | 6/2006 | Newkirk et al. |
| 7,128,300 B2 | * | 10/2006 | Frick ........................... 248/418 |
| 7,197,109 B2 | | 3/2007 | Rotondo et al. |
| 2004/0199996 A1 | | 10/2004 | Newkirk et al. |
| 2005/0000019 A1 | | 1/2005 | Newkirk et al. |

FOREIGN PATENT DOCUMENTS

| | | |
|---|---|---|
| DE | 31 00 819 A1 | 7/1982 |
| DE | 37 01 172 A1 | 7/1988 |
| DE | 93 09 467.1 U1 | 7/1988 |
| DE | 93 10 102.3 U1 | 11/1993 |
| WO | WO 87/07688 A1 | 12/1987 |
| WO | WO 92/18085 | 10/1992 |
| WO | WO 98/33419 A1 | 8/1998 |
| WO | WO 00/09061 | 2/2000 |
| WO | WO2005/037164 | 4/2005 |
| WO | WO 2005/037166 A2 | 5/2005 |

OTHER PUBLICATIONS

International Search Report based on PCT/US2004/033648 completed Jul. 9, 2008.

* cited by examiner ns mayus 7,849,978 B2

BRAKE SYSTEM FOR PATIENT CARE EQUIPMENT SUPPORT ARM

CROSS REFERENCE TO RELATED APPLICATIONS

This application is a U.S. national application under 37 C.F.R. §371(b) of International Application Serial No. PCT/US2004/033648 filed Oct. 12, 2004, which claims priority under 35 U.S.C. 119(e) to U.S. Provisional Application Ser. No. 60/510,756, entitled "PATIENT EQUIPMENT SUPPORT SYSTEM," filed Oct. 13, 2003, which is expressly incorporated by reference herein.

FIELD OF THE INVENTION

The present disclosure relates to a system for supporting patient care equipment, and more particularly relates to a brake system for use with patient care equipment support system.

BACKGROUND AND SUMMARY OF THE INVENTION

Hospitalized patients often require patient care equipment to be in close proximity during hospital care. Such patient care equipment may include heart monitoring equipment, medical gas delivery equipment, infusion pumps, intravenous bags, equipment monitors, defibrillators, and other patient care equipment, many of which directly connect to the patient via lines or tubes.

The present invention comprises one or more of the following features or elements in the appended claims or combinations thereof.

A support structure is provided typically to be at the head end of a patient support device. The support structure may be configured to be mounted to extend between a hospital floor and ceiling, or upwardly from a hospital floor or downwardly from a hospital ceiling, or it may be configured to extend outwardly from a hospital wall or be embedded in the wall. The support structure may be positioned adjacent a hospital wall or spaced therefrom. An arm extends from the support structure and is pivotally movable relative to the structure, typically in a horizontal plane. The arm may be telescoping or fixed in length and comprise a first portion having a mount end pivotably mounted to the support structure and a distal end extending away from the support structure. The first portion is pivotable about a pivot axis, and a second portion is coupled to the distal end of the first portion and may be configured to telescope relative to the first portion.

A patient care equipment column may be supported by the second portion, the patient care equipment column providing either mounting capabilities for patient care equipment or a service head for patient care equipment, or both. Patient care equipment may be mounted or coupled to an equipment support, and/or patient care equipment may be coupled to any one or more of the services provided by one or more service heads. The patient care equipment column may be pivotable about a vertical axis passing through the distal end of the arm.

The support structure may be integrated with or part of a headwall and/or a bed locator. The support structure and/or arm and/or service head and/or headwall may have service outlets, such as for delivery of medical gases or suction, delivery of electrical power, and transmission of data.

Additional telescoping or fixed-length arms may be provided, and may be mounted to the support structure for horizontal pivotable movement about the same pivot axis, or about different axes. Such additional arms may carry a service head, a monitor, and/or patient monitoring equipment.

In some illustrative embodiments, a console or head wall unit is provided, the console providing cabinets for housing any one of the service head, the monitor, and the equipment support when these are in their respective storage positions.

Illustratively, a brake system is provided for impeding the pivoting movement of at least one of the arms when the brake system is actuated. In the illustrated embodiment, the brake system includes a pivot member, such as a tube or an arbor, coupled to the arm for rotation therewith about an axis. A brake is movable between a braking position engaging the pivot member with sufficient force to impede the pivoting movement of the arm and a releasing position allowing pivoting movement of the arm. An actuator is coupled to the brake to move the brake between the braking and releasing positions in response to an input from a user. Typically, the pivot member will be a tube mounted to the arm generally concentric with the axis of rotation of the arm.

In some embodiments, the brake includes a strap configured to be wrapped around a portion of the pivot member and a linear actuator coupled to the strap. In some other embodiments, the brake includes a brake pad engageable with the pivot member, a caliper arm carrying the brake pad and a linear actuator coupled to the caliper arm for moving the brake pad into and out of engagement with the pivot member in response to a user input.

In alternative embodiments, the brake includes a gear mounted generally concentrically to the pivot member for rotation therewith, a caliper arm having a tooth and a linear actuator coupled to the caliper arm for moving the tooth into and out of engagement with the pivot member-mounted gear in response to a user input.

Features of the present disclosure will become apparent to those skilled in the art upon consideration of the following detailed description of illustrative embodiments exemplifying the best mode of carrying out the present disclosure as presently perceived.

BRIEF DESCRIPTION OF THE DRAWINGS

The detailed description particularly refers to the accompanying figures, in which.

DESCRIPTION OF THE ILLUSTRATIVE EMBODIMENTS

For the purposes of promoting an understanding of the principles of the present invention, reference will now be made to a number of illustrative embodiments shown in the accompanying drawings and the following description.

Figure 1:
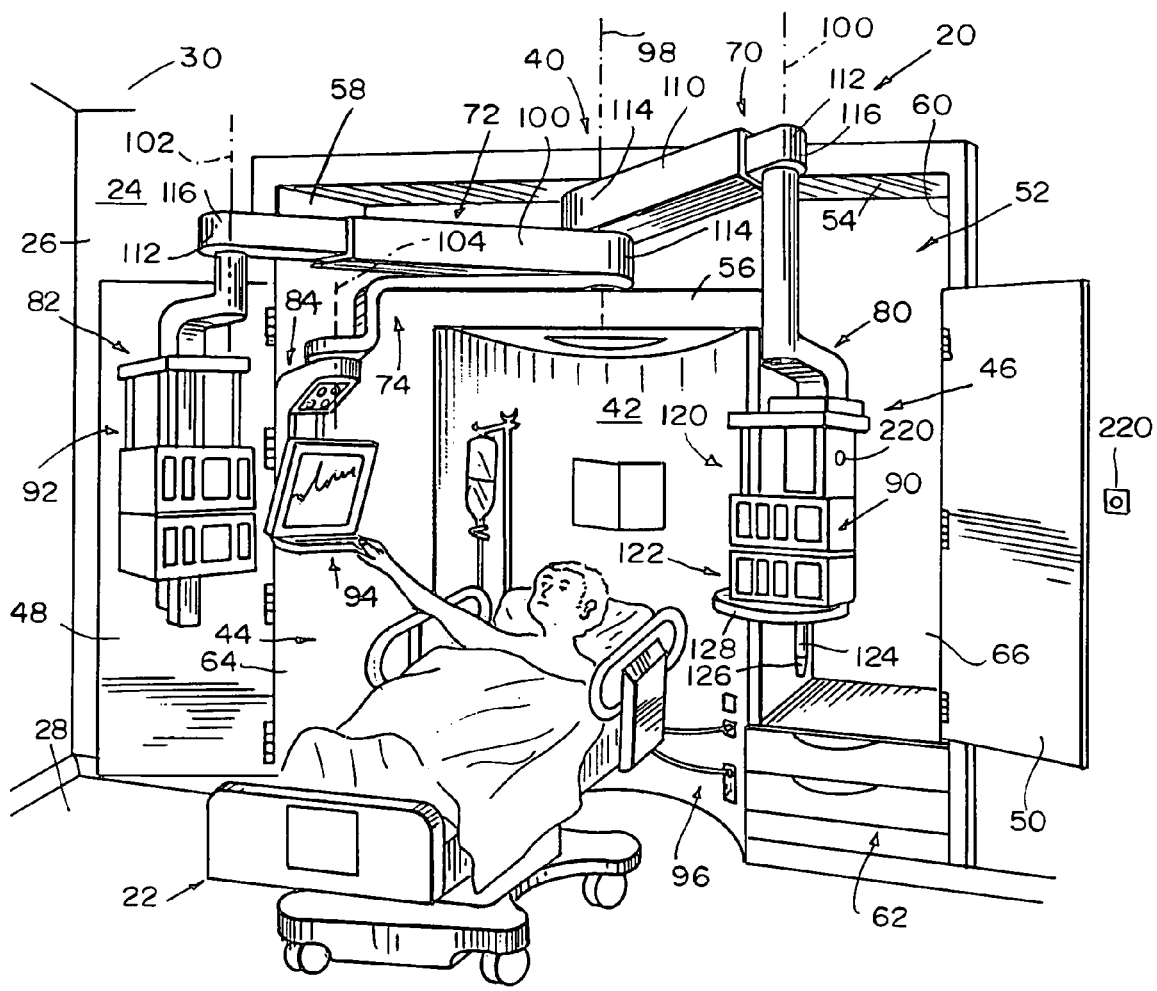
FIG. 1 is a perspective view of a patient care equipment support system and a hospital bed positioned adjacent thereto, and showing a headwall, cabinets on both sides of the headwall and a plurality of radial arms supporting respective patient care equipment columns.

FIG. 1 shows a patient care equipment support system 20 and a patient support device 22 positioned in front of the equipment support system 20. The patient support device 22 is illustratively a hospital bed positioned in a patient room 24 of a hospital or healthcare facility. However, it should be understood that the equipment support system 20 may very well be used in conjunction with other patient support devices, such as, for example, stretchers, ambulatory care chairs, etc. Also, it should be understood that the equipment support system 20 may be used in different settings such as, for example, intensive care rooms, operating rooms, and physician offices.

The equipment support system 20 includes a console 40 including a headwall 42 having cabinets 44, 46 positioned on the opposite sides thereof. Illustratively, the cabinets 44, 46 have access doors 48, 50. Alternatively, the cabinets 44, 46 may be without doors. Also, it is within the scope of the present disclosure to utilize other types of doors such as bi-fold doors or pocket doors. Further, it is within the scope of the present disclosure for the console 40 to have only one cabinet or to have no cabinets at all. The console 40 includes an upper space 52 bounded by a top wall 54, a bottom wall 56 and side walls 58, 60. In some embodiments, the upper space 52 may be dispensed with.

A plurality of drawers 62 are illustratively positioned under the cabinet 46 for providing additional storage space. Alternatively, the drawers 62 may be replaced with a supply cart or a pull-out stool (not shown) for use by a caregiver. In some embodiments, the pull-out stool is movable between a raised use position and a lowered storage position for storage under the cabinet 46.

Illustratively, the headwall 42, the cabinets 44, 46 and the drawers 62 are built into the wall 26 of the patient room 24 such that the front surfaces of the headwall 42, the cabinets 44, 46 and the drawers 62 are substantially flush with the wall 26. However, it is should be understood that the equipment support system 20 could be positioned to jut outwardly from the wall 26, or, alternatively, spaced apart from the wall 26 as a freestanding structure. Also, the equipment support system 20 may be configured to extend between the floor 28 and the ceiling 30 of the hospital room 24, or may be configured to extend upwardly from the floor 28 or extend downwardly from the ceiling 30.

The equipment support system 20 includes a plurality of radial arms 70, 72, 74 extending outwardly from a support structure 76 (shown in FIG. 2) of the headwall 42. Alternatively, the radial arms 70, 72, 74 may be suspended from the ceiling 30 of the hospital room 24. Each radial arm 70, 72, 74 carries a patient care equipment column 80, 82 and 84 at a distal end thereof. Each column 80, 82, 84, in turn, carries some type of patient care equipment 90, 92 and 94.

As used in the description and claims, the words "arm" or "radial arm" generally refer to a horizontally disposed structure, and the word "column" generally refers to a vertically disposed structure mounted on a radial arm. However, these definitions should not in any way be construed as limiting to the possibility of embodiments.

Some examples of the patient care equipment 90, 92 and 94 are heart monitoring equipment, medical gas delivery equipment, infusion management systems, intra-venous pumps, intra-venous bags, equipment monitors, patient care monitors, defibrillators, satellite modules, service connectors, and the like, many of which are directly connected to the patient via lines or tubes. In addition, the headwall 42 may include service connectors 96. Some examples of service connectors are electrical ports, medical gas ports (such as oxygen, nitrogen, etc), vacuum ports and communication ports (such as video, audio, data, etc).

The radial arms 70, 72, 74 are mounted to the support structure 76 to pivot about a generally vertical pivot axis 98. Although, the radial arms 70, 72, 74 are mounted to the support structure 76 to pivot about the common pivot axis 98, the radial arms 70, 72, 74 may very well be mounted to pivot about separate pivot axes (not shown). For example, the radial arms 70, 72, 74 may be spaced apart along the length dimension of the headwall 42 such that the arms 70, 72, 74 have parallel spaced apart pivot axes. Alternatively, the radial arms 70, 72, 74 may be positioned on separate spaced apart walls in the hospital room 24.

Each column 80, 82, 84 is pivotable about a second vertical axis 100, 102, 104 that is parallel to and spaced apart from the common pivot axis 98. Such dual pivoting movement permits each arm 70, 72, 74 to be accessible from a wide range of locations in the hospital room 24. In addition, the first and second radial arms 70, 72 are configured to be telescoping to provide greater flexibility and movement of the arms 70, 72 and the attached columns 80, 82. The third radial arm 74, however, is fixed length.

Each telescoping arm 70, 72 includes a first segment 110 and a second segment 112 that telescopes horizontally into and out of the first segment 110. Each first segment 110 has a mount end 114 coupled to the headwall support structure 76 for pivoting movement about the common pivot axis 98. Each second segment 112 has a distal end 116 coupled to the respective patient care column 80, 82.

The first telescoping arm 70, the associated column 80 and the patient care equipment 90 can pass around both the second and third arms 72, 74, the associated columns 82, 84 and the patient care equipment 92, 94. Likewise, the second telescoping arm 72, the associated column 82 and the patient care equipment 92 can pass around the third arm 74, the associated column 84 and the patient care equipment 94. This feature provides the option of positioning the first arm 70 on either side of the second and third arms 72, 74 and the second arm 72 on either side of the third arm 74, thereby giving the caregiver flexibility in setting up the patient care equipment about a patient. Illustratively, the longer reaching arms are positioned vertically above the shorter arms, facilitating movement of the arms past each other.

Illustratively, the upper space 52 extends horizontally for substantially the entire length of the console 40. Also, the upper space 52 is of sufficient depth to allow the radial arms 70, 72, 74 to be positioned in their storage positions inside the upper space 52. The interior regions 64, 66 of the cabinets 44, 46 communicate with the upper space 52 so that when the radial arms 70, 72, 74 are in their storage positions, the columns 80, 82 and 84 and the associated patient care equipment 90, 92 and 94 are stowed inside the respective storage cabinets 44, 46. Illustratively, the console 40 is configured such that the radial arms 70, 72, 74, the columns 80, 82 and 84 and the associated patient care equipment 90, 92 and 94 can be stored completely within the console 40.

Illustratively, the patient care column 80 includes an upper segment 120 and a lower segment 122 that telescopes vertically relative to the upper segment 120 under the power of an electric motor, such as a linear actuator, housed in the upper segment 120. A switch for operating the electric motor may be provided either on the patient care column 80 or on a remote control. The lower segment 122 of the patient care column 80 includes a post receiver 124 for receiving a mounting post 126 of a patient care equipment support 128. The patient care equipment 90 is supported on the patient care equipment support 128, which, in turn, is supported on the lower segment 122 of the patient care column 80.

The vertical telescoping movement of the lower segment 122 relative to the upper segment 120 permits the patient care equipment support 128 to be raised and lowered for facilitating the loading of the patient care equipment 90 thereon. Also, such vertical movement permits optimal positioning of the patient care equipment 90 relative to the patient support device 22. In addition, such vertical movement permits the docking of the patient care equipment support 128 with a post receiver (not shown) mounted on the patient support device 22 or in one of the cabinets 44, 46. An illustrative patient care equipment support system of this type is described in U.S. Patent Application Publication No. US 2004/0199996 A1 which is hereby incorporated by reference.

Figure 2:
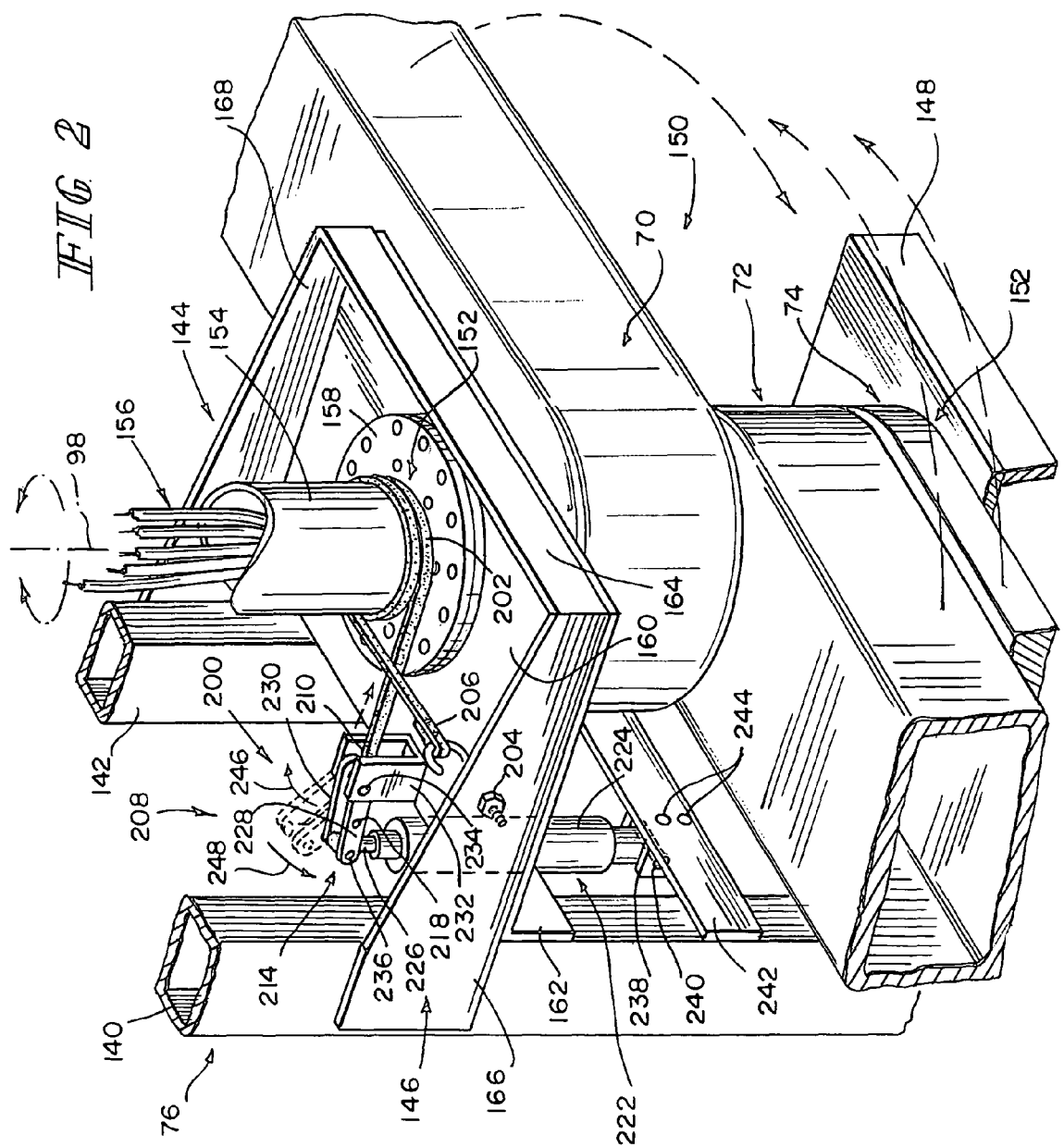
FIG. 2 is a perspective view of a headwall support structure supporting the radial arms and a brake system for selectively impeding the pivoting movement of at least one of the radial arms relative to the headwall support structure when the brake system is actuated.

FIG. 2 shows the support structure 76 supporting the radial arms 70, 72, 74 for pivoting movement about the common pivot axis 98. Illustratively, the support structure 76 includes a pair of laterally, spaced apart, vertically extending members 140, 142. An arm mount 144 extends laterally between the vertically extending members 140, 142 near the ceiling 30. The arm mount 144 includes an upper platform 146 and a lower platform 148. As shown in FIG. 2, the radial arms 70, 72, 74 are received in a space 150 bounded by the upper and lower platforms 146, 148.

In some embodiments, the vertically extending members 140, 142 extend between the floor 28 and the ceiling 30. The floor 28 and ceiling 30 near the headwall support structure 76 may require additional reinforcement in order to support the weight of the radial arms 70, 72, 74 and the associated columns 80, 82, 84 and the patient care equipment 90, 92, 94.

The upper and lower platforms 146, 148 each have a central bore 152. Each arm 70, 72, 74 includes a pivot member, such as a tube or an arbor, which extends through the central bores 152 in the platforms 146, 148 so that the arms 70, 72, 74 can each individually pivot about the common pivot axis 98. Typically, the pivot member will be a tube mounted to the associated arm 70, 72, 74 generally concentric with the axis of rotation 98 thereof. Only one pivot tube 154 coupled to the arm 70 is shown. The pivot tubes coupled to the arms 72, 74 are not shown. The term "tube" used in the specification and claims generally refers to a cylindrical member such as a shaft, an arbor, etc.

As shown in FIG. 2, the pivot tube 154 coupled to the arm 70 extends upwardly through the central bore 152 in the upper platform 146. A plurality of service lines 156 are routed from the ceiling 30 through the support structure 76, the arms 70-74 and the columns 80-84 to the associated patient care equipment 90-94. The support structure 76 includes thrust bearings 158 for supporting the weight of the arms 70-74, the associated columns 80-84 and the patient care equipment 90-94.

The upper and lower platforms 146, 148 are similarly constructed. The description below of the upper platform 146 is descriptive of both the upper and lower platforms 146, 148. Illustratively, the upper platform 146 includes an outwardly extending shelf 160, a back wall 162 extending along a back edge of the shelf 160, a front wall 164 extending along a front edge of the shelf 160 and a pair of side walls 166, 168 extending along side edges of the shelf 160.

Illustratively, a brake 200 is provided for impeding the pivoting movement of the arm 70 about the pivot axis 98 when the brake 200 is actuated. The brake 200 includes a strap or belt 202 coupled to a hook 204 at a first end 206 thereof and coupled to a strap tightener 208 at a second end 210 thereof. The strap 202 is partially wrapped around the pivot tube 154 which is fixedly attached to the arm 70 for rotation therewith. Illustratively, the strap 202 is made of rubber, metal or composite having relatively high coefficient of friction. The hook 204 is bolted to the side wall 166 of the upper platform 146. The first end 206 of the strap 202 forms a loop for engagement with the hook 204. The strap tightener 208 includes an over-the-center linkage 214. The second end 210 of the strap 202 forms a loop for engagement with a pin 218 of the over-the-center linkage 214.

When the strap tightener 208 is in a strap-tightening position, the strap 202 is pulled tightly to constrict around the pivot tube 154 fixedly mounted to the arm 70 such that the pivoting movement of the arm 70 is impeded. When a caregiver desires to move the arm 70, the caregiver operates a user input device 220 to move the strap tightener 208 to a strap-releasing position to loosen the strap 202 around the pivot tube 154 to free the arm 70 to pivot about the pivot axis 98. The user input device 220 may be a button, a handle, lever, switch, knob, and the like. The user input device 220 may be located at any convenient location for access by a caregiver. Thus, the user input device 220 may be located on the patient care column 80 at about the shoulder-height position. Alternatively, the user input device 220 may be located at a location remote from the column 80 such as, for example, on the wall 26 of the patient room 24 or on a remote control device. In the embodiment shown in FIGS. 1 and 2, the user input device 220 is located on the column 80 and on the wall 26.

Illustratively, the strap tightener 208 includes a linear actuator 222 coupled to the over-the-center linkage 214. The linear actuator 222 includes a housing 224 and a piston 226 reciprocably mounted therein. The over-the-center linkage 214 includes two links 228, 230 arranged substantially in parallel. At one end, the links 228, 230 are pivotably mounted to a u-shaped bracket 232 via two spaced-apart pins 234. The u-shaped bracket 232 is mounted on the shelf 160 of the headwall support structure 76. At the other end, the links 228, 230 are pivotably mounted to the piston 226 of the linear actuator 222 via a pin 236. The housing 224 of the linear actuator 222 is pivotably mounted to a bracket 238 via a pin 240. The bracket 238 is mounted to a horizontally extending cross member 242 by fasteners 244. The cross member 242 is mounted to the vertically extending members 140, 142 of the headwall support structure 76. The pin 218 of the over-the-center linkage 214 to which the second end 210 of the strap 202 is attached is located intermediate of the pins 234 at one end of the links 228, 230 and the pin 236 at the other end of the links 228, 230.

When the linear actuator 222 is deactivated, the tightener 208 is in the strap-tightening position (shown in solid in FIG. 2) preventing the pivot tube 154 and the arm 70 from rotating about the pivot axis 98. In this position, the piston 226 is retracted back into the housing 224 and the links 228, 230 are just below the center point at which the links 228, 230 and the strap 202 are generally horizontal. When the linear actuator 222 is activated, the tightener 208 moves to the strap-releasing position (shown in phantom in FIG. 2). In this position, the piston 226 extends upwardly from the housing 224. As the piston 226 extends upwardly, the links 228, 230 are pivoted about the two spaced-apart pins 234 in a clockwise direction 246. As the links 228, 230 pivot in the clockwise direction 246, the pin 218 to which the second end 210 of the strap 202 is attached moves closer to the pivot tube 154, thereby releasing the tension in the strap 202. When the tension in the strap 202 is released, the pivot tube 154 and the arm 70 are freed to pivot about the pivot axis 98.

When the linear actuator 222 is again deactivated, the tightener 208 moves back to the strap-tightening position (shown in solid in FIG. 2) to impede the pivot tube 154 and the arm 70 from rotating about the pivot axis 98. In the strap-tightening position, the piston 226 is retracted back into the housing 224 and the links 228, 230 are pivoted in a counterclockwise direction 248. As the links 228, 230 pivot in the counterclockwise direction 248, the pin 218 to which the second end 210 of the strap 202 is attached moves away from the pivot tube 154, thereby increasing the tension in the strap 202. When the tension in the strap 202 is increased, the pivot tube 154 and the arm 70 are restricted from pivoting about the pivot axis 98. As the links 228, 230 pass the center point at which the links 228, 230 and the strap 202 are generally horizontal, the tension in the strap 202 causes the pin 218 to which the second end 210 of the strap 202 is attached to exert downward pressure on the piston 226 of the linear actuator 222, effectively preventing accidental release of the tension in the strap 202 until the linear actuator 222 is again activated. This fail-safe feature also prevents accidental release of the tension in the strap 202 in the event of power or equipment failure.

In the illustrative embodiment, when the strap tightener 208 is in the strap-tightening position, a caregiver may still be able to pivot the arm 70 about the pivot axis 98 with a predetermined amount of force. Thus, the arm 70 is able to be moved even in the event of a power or equipment failure. However, during normal operation, a caregiver engages the button 222 to loosen the strap 202 and then moves the arm 70 and the column 80 to the desired position. When the arm 70 and the column 80 reach the desired position, the button 222 is released and the strap tightener 208 is again reactivated.

Figure 3:
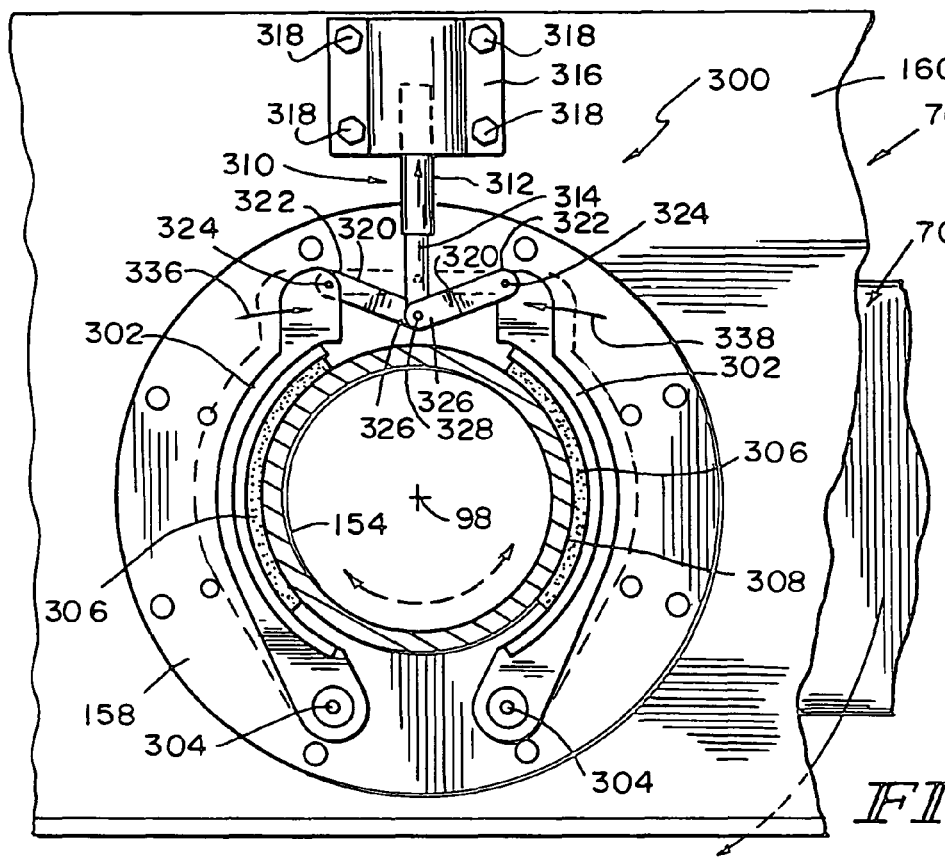
FIGS. 3 and 4 are perspective views of alternative embodiments of the FIG. 2 brake system.

FIG. 3 shows a second embodiment 300 of the brake to selectively impede the pivoting movement of the arm 70. The brake 300 includes a pair of caliper arms 302 that pivot about respective pins 304. The pins 304 are mounted to the shelf 160 of the headwall support structure 76. The caliper arms 302 may have associated brake pads 306 coupled thereto for engagement with the outer surface 308 of the pivot tube 154 carried by the arm 70. A linear actuator 310 is illustratively provided for moving the caliper arms 302 between a brake-engaging position shown in FIG. 3, where the brake pads 306 are pressed against the pivot tube 154 so that the pivot tube 154 and the radial arm 70 are impeded from pivoting about the pivot axis 98, and a brake-releasing position shown in phantom in FIG. 3, where the brake pads 306 disengage from the pivot tube 154 so that the pivot tube 154 and the radial arm 70 are permitted to pivot about the pivot axis 98.

The linear actuator 310 includes a housing 312 and a plunger 314 reciprocably mounted therein. The housing 312 of the linear actuator 310 is mounted to a bracket 316. The bracket 316 is mounted on the shelf 160 of the headwall support structure 76 by fasteners 318. A pair of links 320 is provided. At one end 322, the links 320 are pivotably mounted to the caliper arms 302 via respective pivot pins 324. At the other end 326, the links 320 are pivotably mounted to the plunger 314 of the linear actuator 310 via a pivot pin 328.

In the brake-engaging position shown in FIG. 3, the plunger 314 extends outwardly from the housing 312 causing the left link 320 to pivot about the common pivot pin 328 in a clockwise direction and the right link 320 to pivot about the common pivot pin 328 in a counterclockwise direction. Such pivoting movement of the links 320 causes the pivot pins 324 to move in opposite directions 336, 338 toward each other to, in turn, cause the calipers arms 302 to close so that the brake pads 306 are pressed against the outer surface 308 of the pivot tube 154 to impede the pivoting movement of the arm 70.

In the brake-releasing position shown in phantom in FIG. 3, the plunger 314 retracts into the housing 312 causing the left link 320 to pivot about the common pivot pin 328 in a counterclockwise direction and the right link 320 to pivot about the common pivot pin 328 in a clockwise direction. Such pivoting movement of the links 320 causes the pivot pins 324 to move in opposite directions away from each other to, in turn, cause the calipers arms 302 to spread apart so that the brake pads 306 disengage from the outer surface 308 of the pivot tube 154 to permit the pivoting movement of the arm 70.

Figure 4:
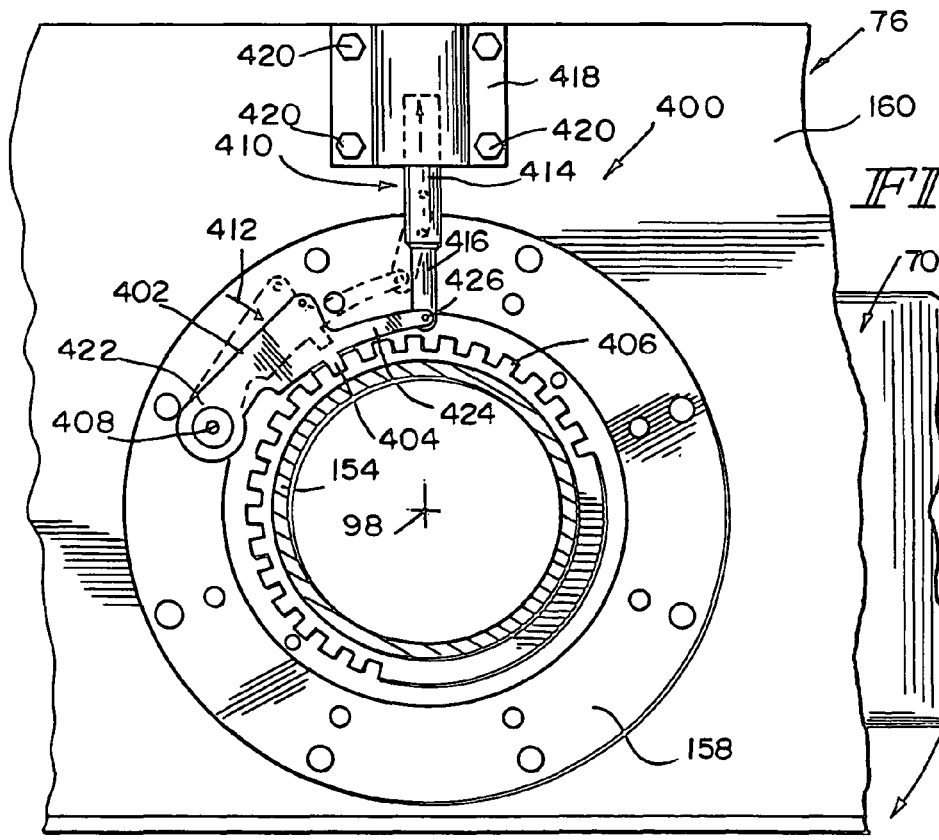

FIG. 4 shows a third embodiment 400 of the brake to selectively prevent the pivoting movement of the arm 70. The brake 400 includes a caliper arm 402 having at least one tooth 404 formed thereon and a gear 406 mounted on the pivot tube 154 for rotation therewith. In the illustrated embodiment, the gear 406 has teeth only over a section of the outer periphery thereof. The caliper arm 402 pivots about a pivot pin 408 mounted to the shelf 160 of the headwall support structure 76. A linear actuator 410 is illustratively provided for moving the caliper arm 402 between a brake-engaging position shown in FIG. 4, where the tooth 404 engages the gear 406 so that the pivot tube 154 and the radial arm 70 are prevented from pivoting about the pivot axis 98, and a brake-releasing position shown in phantom in FIG. 4, where the tooth 404 disengages from the gear 406 so that the pivot tube 154 and the radial arm 70 are permitted to pivot about the pivot axis 98. The caliper arm 402 is spring loaded in a direction 412 causing the tooth 404 to engage the gear 406 to prevent pivoting movement of the pivot tube 154 and the arm 70.

The actuator 410 includes a plunger 414 reciprocably mounted in the actuator housing. The plunger 414 is coupled to the caliper arm 402 by a pivotable link 416. The housing of the linear actuator 410 is secured to the shelf 160 of the headwall support structure 76 by a bracket 418. The bracket 418 is mounted on the shelf 160 by fasteners 420. At one end 422, the caliper arm 402 pivots about the pivot pin 408. At the other end 424, the caliper arm 402 is pivoatably coupled to the pivotable link 416 via a pivot pin 426.

In the brake-engaging position shown in FIG. 4, the plunger 414 extends outwardly from the actuator housing causing the caliper arm 402 to move toward the gear 406 so that the tooth 404 engages the gear 406 mounted on the pivot tube 154 to prevent the pivoting movement of the arm 70. In the brake-releasing position shown in phantom in FIG. 4, the plunger 414 retracts into the actuator housing causing the caliper arm 402 to move away from the gear 406 so that the tooth 404 disengages from the gear 406 to permit the pivoting movement of the arm 70.

While the invention has been illustrated and described in detail in the foregoing drawings and description, the same is to be considered as illustrative and not restrictive in character, it being understood that only illustrative embodiments thereof have been shown and described and that all changes and modifications that come within the spirit of the invention are desired to be protected.

The invention claimed is:

1. A patient care equipment support system comprising:
   a support structure extending between a floor and a ceiling of a hospital room, the support structure having a service outlet for delivery of a medical gas, the support structure having an arm mount including an upper platform and a lower platform, the upper and lower platforms each being closer to the ceiling than to the floor;
   an arm coupled to the support structure and supported in the hospital room for pivoting movement about a generally vertical axis, the arm having an interior region, a proximal end of the arm being situated between the upper and lower platforms,
   a column coupled to the arm for movement therewith, the column configured to support patient care equipment, and
   a brake located outside the interior region of the arm and movable between a braking position to impede the pivoting movement of the arm and a releasing position allowing pivoting movement of the arm, at least one service line that provides a service to the patient care equipment extending from outside the arm into the interior region of the arm passed the brake and extending within the interior region of the arm away from the brake toward an end of the arm.

2. The system of claim 1, wherein the brake normally impedes the pivoting movement of the arm, and the brake allows the pivoting movement of the arm when the brake is deactivated in response to a user input.

3. The system of claim 2, wherein the brake is deactivated by a user input device, and the user input device is mounted on the column.

4. The system of claim 2, wherein the brake is deactivated by a user input device, and the user input device is mounted remote from the column.

5. The system of claim 1, comprising a pivot member coupled to the arm for rotation therewith about the axis, the pivot member being generally concentric with the axis.

6. The system of claim 5, wherein the brake includes a strap configured to be wrapped around a portion of the pivot member.

7. The system of claim 6, wherein the brake includes a linear actuator coupled to the strap, the linear actuator having a strap-tightening position where the arm is impeded from pivoting about the axis and a strap-releasing position where the arm is permitted to pivot about the axis.

8. The system of claim 5, wherein the brake includes a brake pad engageable with the pivot member.

9. The system of claim 8, wherein the brake includes a linear actuator coupled to the brake pad, the linear actuator having a brake pad-engaging position where the arm is impeded from pivoting about the axis and a brake pad-releasing position where the arm is permitted to pivot about the axis.

10. The system of claim 9, wherein the brake includes a caliper arm carrying the brake pad, and the linear actuator is coupled to the caliper arm for moving the brake pad into and out of engagement with the pivot member in response to a user input.

11. The system of claim 5, wherein the brake includes a gear mounted generally concentrically to the pivot member for rotation therewith.

12. The system of claim 11, wherein the brake includes a caliper arm having a tooth for selectively engaging the gear mounted to the pivot member to prevent pivoting movement of the arm about the axis.

13. The system of claim 12, wherein the brake includes a linear actuator coupled to the caliper arm for moving the tooth into and out of engagement with the pivot member-mounted gear in response to a user input.

14. The system of claim 1, wherein the arm is a telescoping arm.

15. The system of claim 1, wherein the arm is a fixed-length arm.

16. The system of claim 1, wherein the arm extends outwardly from a headwall support structure.

17. The system of claim 1, wherein the arm is supported by a ceiling structure.

18. A patient care equipment support system comprising:
   a support structure extending between a floor and a ceiling of a hospital room, the support structure having a service outlet for delivery of a medical gas, the support structure having an arm mount including an upper platform and a lower platform, the upper and lower platforms each being closer to the ceiling than to the floor;
   an arm coupled to the support structure and supported in the hospital room for pivoting movement about a generally vertical axis, the arm having an interior region, a proximal end of the arm being situated between the upper and lower platforms,
   a column coupled to the arm for movement therewith, the column configured to support patient care equipment, a pivot member coupled to the arm for rotation therewith about the axis, the pivot member being generally concentric with the axis,
   a brake located outside the interior region of the arm and movable between a braking position engaging the pivot member to impede the pivoting movement of the arm and a releasing position allowing pivoting movement of the arm, at least one service line that provides a service to the patient care equipment extending from outside the arm into the interior region of the arm passed the brake and extending within the interior region of the arm away from the brake toward an end of the arm, and
   an actuator coupled to the brake to move the brake between the braking and releasing positions in response to an input from a user.

19. The system of claim 18, wherein the brake includes a strap configured to be wrapped around a portion of the pivot member and a linear actuator coupled to the strap, the linear actuator having a strap-tightening position where the arm is impeded from pivoting about the axis and a strap-releasing position where the arm is permitted to pivot about the axis.

20. The system of claim 18, wherein the brake includes a brake pad engageable with the pivot member, a caliper arm carrying the brake pad and a linear actuator coupled to the caliper arm for moving the brake pad into and out of engagement with the pivot member in response to a user input.

21. The system of claim 18, wherein the brake includes a gear mounted to the pivot member for rotation therewith, a caliper arm having a tooth and a linear actuator coupled to the caliper arm for moving the tooth into and out of engagement with the pivot member-mounted gear in response to a user input.

\* \* \* \* \*